US012668768B2

(12) United States Patent
  Hsu et al.

(10) Patent No.: US 12,668,768 B2
(45) Date of Patent: Jun. 30, 2026

(54) CELL CULTURE DEVICE

(71) Applicant: National Taiwan University, Taipei (TW)

(72) Inventors: Yu-Hsiang Hsu, Taipei (TW); Hong-Wen Wang, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 941 days.

(21) Appl. No.: 17/727,664

(22) Filed: Apr. 22, 2022

(65) Prior Publication Data

US 2022/0340853 A1    Oct. 27, 2022

Related U.S. Application Data

(60) Provisional application No. 63/179,536, filed on Apr. 25, 2021.

(51) Int. Cl.
  C12M 1/12      (2006.01)
  B01L 3/00      (2006.01)
      (Continued)

(52) U.S. Cl.
  CPC ............. C12M 25/04 (2013.01); B01L 3/505 (2013.01); C12M 1/22 (2013.01); C12M 23/12 (2013.01);
      (Continued)

(58) Field of Classification Search
  None
  See application file for complete search history.

(56) References Cited

U.S. PATENT DOCUMENTS 6,048,723 A * 4/2000 Banes ................... C12M 35/04
                                                           435/305.4
7,176,016 B2 2/2007 Maher et al.
             (Continued)

FOREIGN PATENT DOCUMENTS

CN          204644371 U      9/2015
CN          209010535 U      6/2019
             (Continued)

OTHER PUBLICATIONS

W.H. Zimmermann et al., "Tissue Engineering of a Differentiated Cardiac Muscle Construct," Circulation Research 2002, Feb. 8, 2002, pp. 223-230.
             (Continued)

*Primary Examiner* — P. Kathryn Wright
(74) *Attorney, Agent, or Firm* — MUNCY, GEISSLER, OLDS & LOWE, P.C.

(57)          ABSTRACT

A cell culture device is provided, which comprises a cavity and a base layer, wherein the base layer is a type of plastic thin film and has a thickness of 1 μm to 100 μm; a second-moment of inertia lower than $6 \times 10^6$ μm$^4$; and a resultant flexural rigidity of $1 \times 10^{-6}$ Pa·m$^4$ to 0.02 Pa·m$^4$. Accordingly, the base layer can produce an out-of-plane strain, and bending deformation can occur. Therefore, a growth space close to in vivo environment is provided by the base layer for the cells when the cells attach to the base layer, thereby promoting the growth and maturation of the cells and tissues.

5 Claims, 12 Drawing Sheets

(51) Int. Cl.
  *C12M 1/22*   (2006.01)
  *C12M 1/32*   (2006.01)
(52) U.S. Cl.
  CPC ...... *C12M 25/14* (2013.01); *B01L 2300/0829*
               (2013.01)

(56)    References Cited

U.S. PATENT DOCUMENTS

| | | | |
|---|---|---|---|
| 7,829,334 | B2 | 11/2010 | Kanzaki et al. |
| 9,452,564 | B2 | 9/2016 | Khine et al. |
| 9,994,812 | B2 | 6/2018 | Kim et al. |
| 10,591,458 | B2 | 3/2020 | Parker et al. |
| 2003/0143727 | A1 | 7/2003 | Chang |
| 2009/0170190 | A1 | 7/2009 | Nishi et al. |
| 2015/0125952 | A1* | 5/2015 | Kim .................... A61L 27/3873 |
| | | | 435/396 |
| 2020/0032188 | A1 | 1/2020 | Chou et al. |

FOREIGN PATENT DOCUMENTS

| | | |
|---|---|---|
| CN | 212316137 U | 1/2021 |
| TW | I259203 B | 8/2006 |
| TW | I424058 B | 1/2014 |
| TW | I672374 B | 9/2019 |
| TW | 202016288 A | 5/2020 |

OTHER PUBLICATIONS

Adam J. Engler et al., "Embryonic cardiomyocytes beat best on a matrix with heart-like elasticity: scar-like rigidity inhibits beating," Nov. 15, 2008, pp. 3794-3802, J Cell Sci.

Aida Salameh et al., "Cyclic Mechanical Stretch Induces Cardiomyocyte Orientation and Polarization of the Gap Junction Protein Connexin43", Apr. 8, 2010, pp. 1592-1602, Circulation Research 2010.

Anna Grosberg et al., "Muscle on a chip: In vitro contractility assays for smooth and striated muscle", Journal of Pharmacological and Toxicological Methods, Apr. 12, 2012, pp. 126-135, vol. 65.

Megan L. McCain et al., "Matrix elasticity regulates the optimal cardiac myocyte shape for contractility," Am J Physiol Heart Circ Physiol., Mar. 28, 2014, pp. H1525-H1539.

* cited by examiner

1000

2000

Example 15          Example 16          Example 17          Example 18

CELL CULTURE DEVICE

CROSS REFERENCE TO RELATED APPLICATION

This application claims the benefit of U.S. Provisional Application No. 63/179,536, filed on Apr. 25, 2021. The entirety of the Application is incorporated herein by reference.

BACKGROUND OF THE INVENTION

1. Field of the Invention

The present invention relates to a cell culture device, particularly a cell culture device for culturing myocytes.

2. Description of Related Art

The living and diet habits of modern society have changed. In such a highly competitive environment, problems such as human cardiovascular disease have rapidly increased, and the demand for heart-related drugs has also increased significantly. To lower the barrier of drug discovery and screening, cells cultured in vitro were usually used for mass screening of cardiac drugs. During the drug discovery, cardiomyocytes of animals were used for drug screening, such as rats, hamsters, rabbits, etc. However, the cardiomyocytes of an animal must be isolated from living animals, and animals are genetically different from humans. Therefore, by using human cardiomyocytes differentiated from human induced pluripotent stem cells, the low drug efficacy and toxicity caused by the use of animal cardiomyocytes can be significantly reduced.

Most of the cardiomyocytes are currently cultured in culture dishes or multi-well plates made of plastic materials. However, since the stiffness of plastics is much higher than that of myocytes, culturing myocytes on such materials may lead to incomplete differentiation of stem cells or immature cell morphology. Therefore, even after human-induced pluripotent stem cells are differentiated into cardiomyocytes, they are still not as mature as adult myocytes. They could not reach the contraction behavior similar to in vivo adult myocytes.

To solve the abovementioned problems, the cell culture device provided by the present invention comprises a flexible base layer including microgrooves that generates the out-of-plane strain, such as bending deformation To provide a substrate close to the in vivo cell growth environment, a flexible base layer that can be bent and deformed to compensate for the difference in the substrate stiffness of the conventional cell culture devices and the in vivo cell growth environment is used in the present invention. Thereby, this design can promote the maturation and growth of myocytes, and facilitates the differentiation and development of human-induced pluripotent stem cells into myocytes, and the development of differentiated myocytes into mature cardiomyocytes and tissues.

SUMMARY OF THE INVENTION

A cell culture device is provided, which comprises a cavity including an opening, and a bottom; and a base layer disposed at the bottom of the cavity and closing the bottom; wherein the base layer is made of a plastic thin film.

In one embodiment, a thickness of the base layer is 1 $\mu$m to 100 $\mu$m, a second-moment of inertia is lower than $6\times10^6$ $\mu m^4$, and a resultant flexural rigidity is $1\times10^{-6}$ Pa·m$^4$ to 0.02 Pa·m$^4$.

In one embodiment, the plastic thin-film is at least one selected from the group consisting of polymethyl methacrylate, polypropylene, polystyrene, polyethylene, polyethylene terephthalate, polyvinyl chloride, polydimethylsiloxane, polyurethane, polyacrylamide, and mixtures thereof.

In one embodiment, the thickness of the base layer is 5 $\mu$m to 75 $\mu$m.

In one embodiment, the base layer further includes microgrooves; wherein the microgrooves are arranged parallel to each other or concentrically.

In one embodiment, a width of each of the microgrooves is 5 $\mu$m to 50 $\mu$m, a gap between the adjacent microgrooves is 5 $\mu$m to 50 $\mu$m.

In one embodiment, a depth of each of the microgrooves is 1 $\mu$m to 10 $\mu$m.

In one embodiment, the cell culture device further comprises a hollow spacer disposed under the base layer and contacting with an edge of the base layer.

In one embodiment, the cell culture device further comprises a coating layer formed on the base layer, the coating is at least one selected from the group consisting of matrix hydrogel, collagen, fibronectin, laminin, gelatin, and mixtures thereof.

A cell culture multiwall plate is also provided. The cell culture multi-well plate comprises a main body including an accommodating space and a first surface; and a plurality of abovementioned cell culture devices, wherein each of the plurality of cell culture devices is disposed in the accommodating space; wherein the opening of the cavity of each of the plurality of cell culture device is formed on the first surface.

The cell culture device and the cell culture multi-well plate provided by the present invention are suitable for culturing various types of adherent cells, including adherent cells differentiated from human induced pluripotent stem cells, which is not particularly limited. However, the structure and the characteristics of the cell culture device are especially suitable for culturing myocytes, such as skeletal muscle, smooth muscle, cardiac muscle, etc., and are helping to improve the maturity of myocytes.

DETAILED DESCRIPTION OF THE PREFERRED EMBODIMENT

[Preparation of the Cell Culture Device]

Figure 1:
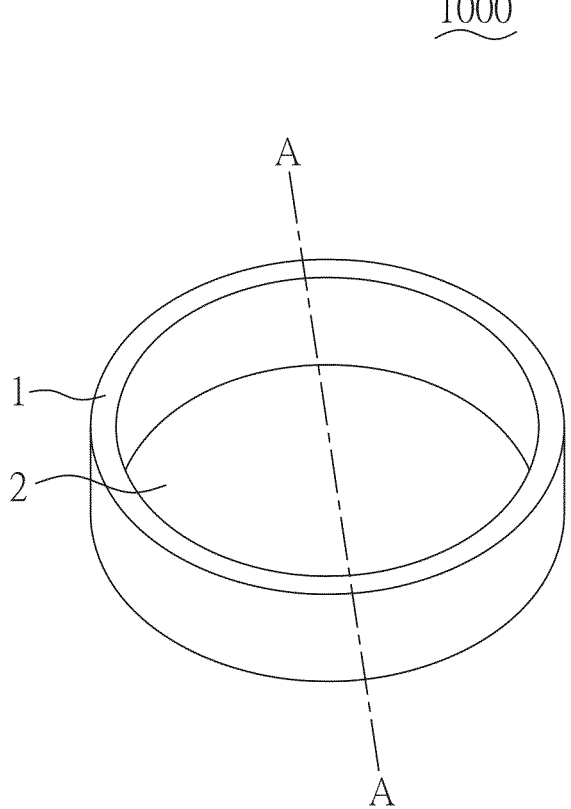
FIG. 1 is a schematic diagram showing the cell culture device of an embodiment of the present invention.
Figure 2:
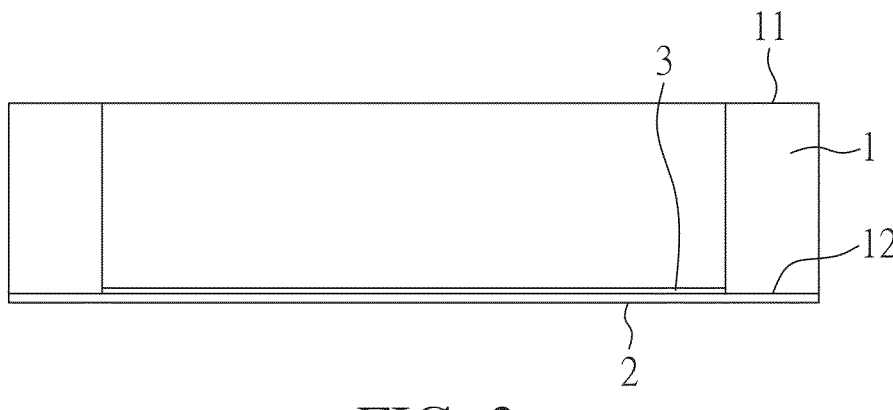
FIG. 2 is a sectional view showing the cell culture device of an embodiment of the present invention.

The cell culture device 1000 provided by the present invention is illustrated in FIG. 1. FIG. 1 shows the schematic diagram and FIG. 2 shows the cross-sectional view along the A-A section line in FIG. 1 of the cell culture device 1000 provided by the present invention. The cell culture device 1000 comprises a cavity 1 and a base layer 2.

The cavity 1 is a hollow cylinder including an opening 11 and a bottom 12 corresponding to the opening 11. The base layer 2 is disposed to the bottom 12 of the cavity 1 and closes the bottom 12. In other embodiments, the shape and size of the cavity 1 are not particularly limited. For example, the shape of the cavity 1 can be square, rectangle, or round, which can be designed according to cell culture requirements.

The base layer 2 is made of a plastic thin film, the thickness thereof may be 1 μm to 100 μm, a second-moment of inertia may be lower than $6 \times 10^6$ μm$^4$, and a resultant flexural rigidity may be $1 \times 10^{-6}$ Pa·m$^4$ to 0.02 Pa·m$^4$. For example, the plastic thin-film can be materials with better biocompatibility such as polymethyl methacrylate (PMMA), polypropylene (PP), polystyrene (PS), polyethylene (PE), polyethylene terephthalate (PET), polyvinyl chloride (PVC), polydimethylsiloxane (PDMS), polyurethane (PU), polyacrylamide (PAM), and mixtures thereof. The base layer 2 used in embodiments and comparative embodiments of the present invention was made of polypropylene, polystyrene, polyvinyl chloride, or polydimethylsiloxane.

Figure 3:
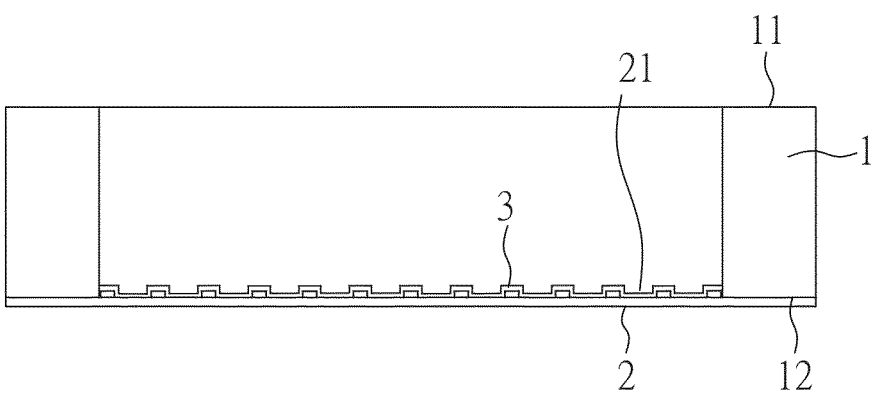
FIG. 3 is a sectional view showing the cell culture device of another embodiment of the present invention.

In other embodiments illustrated in FIG. 3, the base layer 2 includes microgrooves 21 arranged parallel to each other or concentrically. Those microgrooves 21 were prepared by the hot embossing method. The width of each of the microgrooves is 20 μm; the depth of each of the microgrooves is 4 μm, and the gap between the adjacent microgrooves is 20 μm. The microgrooves 21 can further reduce the second-moment of inertia and the resultant flexural rigidity of the base layer 2 to provide a base layer 2 with higher flexibility and bending ability, and can also induce myocytes to align into long and narrow cells.

Furthermore, as shown in FIG. 2 and FIG. 3, the cell culture device 1000 further comprises a coating layer 3. The coating layer 3 is an extracellular matrix to promote cell attachment on the base layer 2. In other embodiments, the coating layer 3 may be other materials that improve cell attachment, such as matrix hydrogel, collagen, fibronectin, laminin, gelatin, and mixtures thereof, which is not particularly limited.

Figure 4:
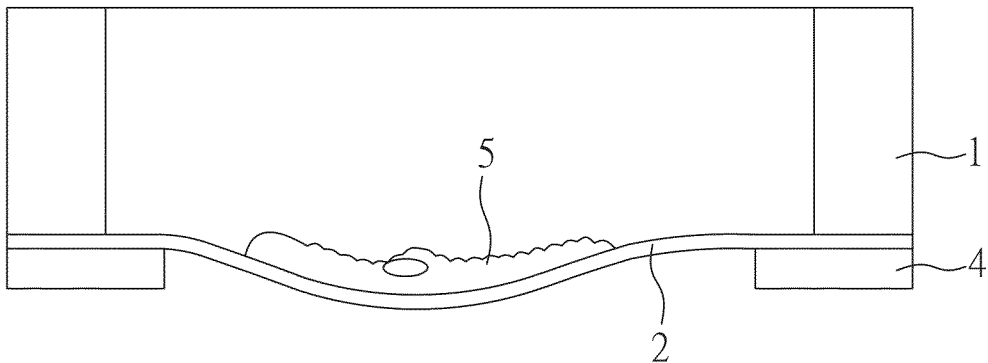
FIG. 4 is a schematic diagram showing the cell culture device of yet another embodiment of the present invention.

The hollow spacer 4 is disposed beneath the base layer 2 and contacts with the edges of the base layer 2 as illustrated in FIG. 4. The hollow spacer 4 is mainly used to prevent the base layer 2 from contacting the underlying working surface or other elements during the process of culturing the cells 5 thereon so that the base layer 2 can generate the out-of-plane strain when the cells 5 are cultured thereon. On the other hand, the hollow spacer 4 also provides an edge that the users can rely on when suctioning and adding reagents, to prevent the user from puncturing the base layer 2.

Figure 5:
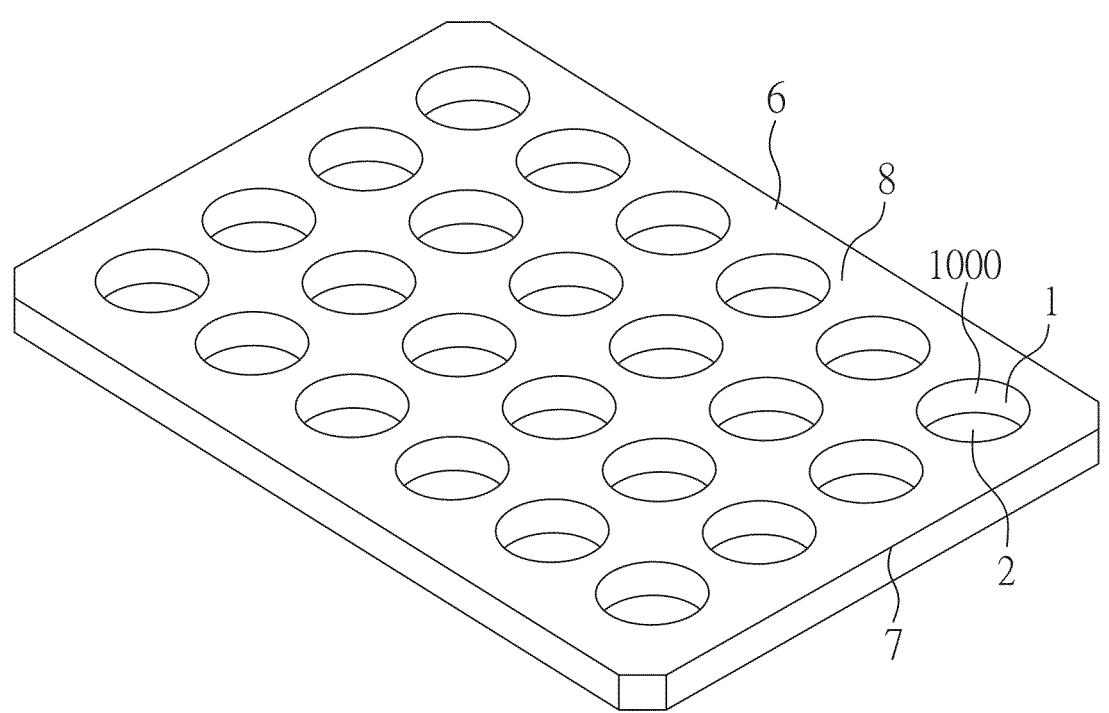
FIG. 5 is a schematic diagram showing the cell culture multi-well plate of an embodiment of the invention.

In other embodiments, a cell culture multi-well plate 2000 illustrated in FIG. 5 is formed with a plurality of the cell culture device 1000, wherein the number and shape of the cell culture device 1000 may be designed according to cell culture requirements without limitation. The cell culture multi-well plate 2000 comprises a main body 6 including an accommodating space 7 and a first surface 8; and a plurality of abovementioned cell culture devices 1000, wherein each of the plurality of cell culture devices 1000 is disposed in the accommodating space 7.

[Cardiomyocyte Culture]

The cells used in the evaluations of the examples and comparative examples of the present invention are cardiomyocytes induced and differentiated from human-induced pluripotent stem cells (hiPSC). The thawed cardiomyocytes were cultured on the 35th day, the cells with different cell densities (10,000 cells/well and 40,000 cells/well) were seeded respectively into cell culture devices with different base layer thicknesses, materials, or micro-grooved structures, and the cells were fixed on the 40th day of culture. Staining and quantitative analysis were then performed.

[Quantitative Analysis of Cardiomyocytes]

The fixed cardiomyocytes were fluorescently stained, wherein the nucleus was stained with Hoechst 33342 (Thermofisher ab 228551); α-actin was stained with anti-α-actin antibody mouse monoclonal IgG1 AT6/172 (Millipore MAB1682) used as the primary antibody stain, and FTTC Conjugated Goat Anti-Mouse IgG antibody (H+L) used as the secondary antibody stain; while F-actin was stained with Alexa Flour Phalloidim.

An inverted fluorescent microscope (IX71, Olympus) was used with different fluorescence filters to excite the nucleus, α-actin, and F-actin stained with dyes in cardiomyocytes.

The captured α-actin fluorescence images were loaded in the built-in software of the inverted fluorescence microscope. Then, the built-in Line profile was used to calculate the length of the sarcomere lengths of the cells.

Furthermore, the software Image J was used to find the boundary of a single cell, and the fluorescence photos taken in advance were loaded. The Threshold function was used to find the cell membrane boundary of the cardiomyocytes, and the cell boundary was displayed using the function of Edges Finder to calculate the area of the cell (A).

In addition, the major axis length and the minor axis length of a single cell were measured by the software Image J, and the following formula was introduced to obtain the ellipticity.

$$\text{Ellipticity} = (\text{major axis length} - \text{minor axis length}) / \text{major axis length}$$

[Data Analysis]

In the present invention, each experiment was repeated three times, and 9 cells were be randomly selected for quantitative analysis in each experiment. The data were analyzed by ANOVA using excel, wherein * means P value≤0.05;  means P value≤0.01; * means P value≤0.001, and indicate that there is a significant difference between the two groups of data, and a P value>0.05 indicates that there is no significant difference between the two groups of data.

[Evaluation of the Effect of Different Thicknesses of the Base Layer on Cardiomyocytes]

First, for the evaluation of the effect of base layers with different thicknesses on high-density cultured cardiomyocytes, please refer to the base layer materials and thicknesses of Examples 1-5 and Comparative Example 1 shown in Table 1. The sarcomere length was used as the evaluation criterion, and the longer the sarcomere length, the more mature the cardiomyocytes.

TABLE 1

| | Material | Thickness (μm) | Cell density (cells/well) | Sarcomere length (μm) |
|---|---|---|---|---|
| Example 1 | PP | 75 | 40000 | 1.75 |
| Example 2 | PP | 30 | 40000 | 1.79 |
| Example 3 | PP | 18 | 40000 | 1.79 |
| Example 4 | PS | 10 | 40000 | 1.79 |
| Example 5 | PVC | 5 | 40000 | 1.91 |
| Comparative example 1 | PDMS | 1000 | 40000 | 1.74 |

Figure 6:
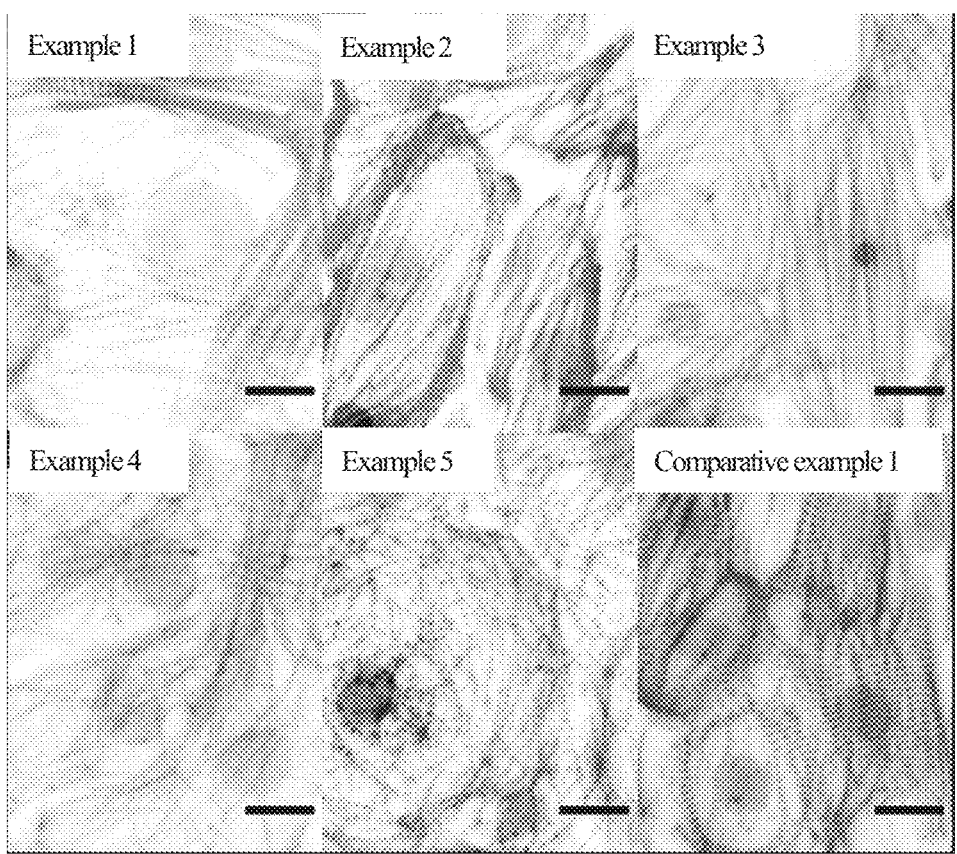
FIG. 6 shows the fluorescent images of the cells of Examples 1 to 5 and Comparative example 1.

Please refer to the fluorescent images of the cells shown in FIG. 6 (scale bar=10 μm), the cell morphology showed that the cardiomyocytes cultured on the flat base layer were mostly round and loosely arranged. Refer to the sarcomere lengths recorded in Table 1, it should be noted that the sarcomere lengths of the cardiomyocytes cultured at high density on the base layer with a thickness of 5 μm to 75 μm were significantly higher than those of the cardiomyocytes in Comparative Example 1. Cardiomyocytes cultured on a base layer with a thickness of 5 μm had the longest sarcomere length. It confirmed that reducing the thickness of the base layer can reduce the flexural rigidity of the film, making the device more suitable for cell culture.

Next, an evaluation of the effects of base layers with different thicknesses on cardiomyocytes cultured at low density was made. The materials and thicknesses of the base layers of Examples 6-10 and Comparative example 2 are shown in Table 2, the sarcomere length, cell area, and cell ellipticity were evaluated and are also shown in Table 2, wherein the closer the cell ellipticity value was to 1, the more slender the cell shape was, and the closer to 0, the more rounded the cell shape was.

TABLE 2

| | Material | Thickness (μm) | Cell density (cells/well) | Sarcomere length (μm) | Cell ellipticity |
|---|---|---|---|---|---|
| Example 6 | PP | 75 | 10000 | 1.64 | 0.58 |
| Example 7 | PP | 30 | 10000 | 1.67 | 0.66 |
| Example 8 | PP | 18 | 10000 | 1.67 | 0.72 |
| Example 9 | PS | 10 | 10000 | 1.67 | 0.72 |
| Example 10 | PVC | 5 | 10000 | 1.67 | 0.72 |
| Comparative example 2 | PDMS | | 10000 | 1.68 | 0.78 |

Figure 7:
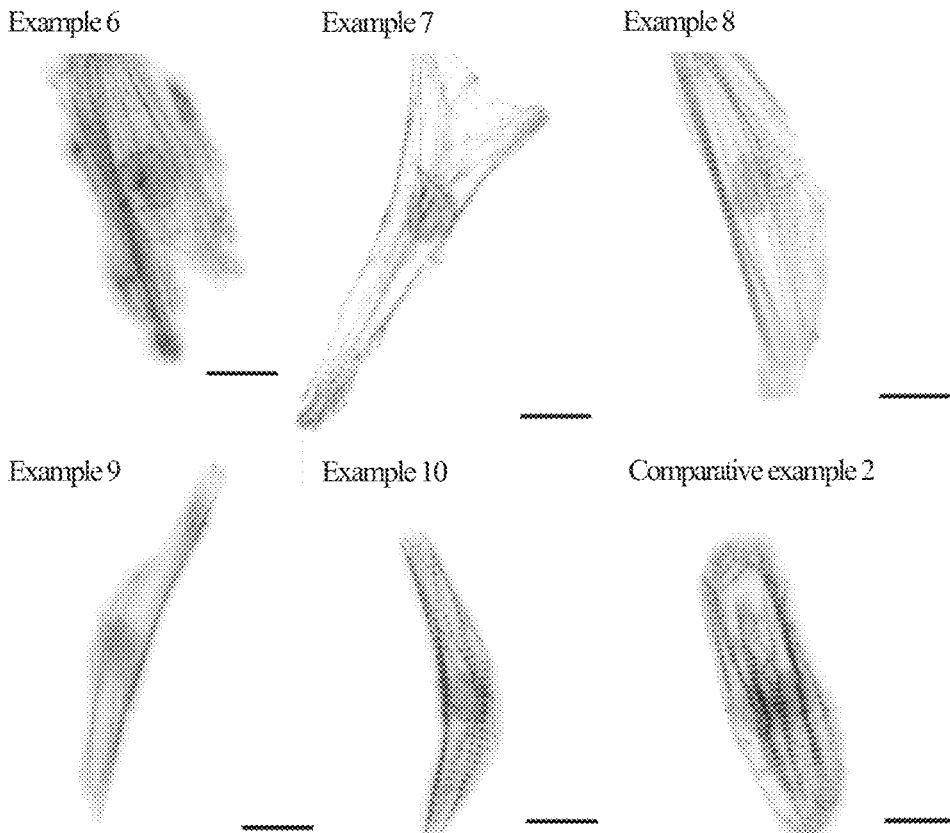
FIG. 7 shows the fluorescent images of the cells of Examples 6 to 10 and Comparative example 2.

FIG. 7 shows the fluorescent images of the cells of Examples 6 to 10 and Comparative example 2 (scale bar=20 μm). After analyzing the fluorescence images, the sarcomere length of the cardiomyocytes was obtained and shown in Table 2. According to the results shown in Table 2, the sarcomere length increased from 1.56 μm to 1.67 μm when the thickness of cardiomyocytes decreased from 75 μm to 5 μm. It is confirmed that reducing the thickness of the base layer for reducing the flexural rigidity of the film can promote the maturation of cardiomyocytes. Next, please refer to the cell ellipticity recorded in Table 2. It can be seen that under the low-density culture of cardiomyocytes, the cardiomyocytes on the base layer of Comparative Example 2 showed an oval shape, and when the thickness of the base layer gradually decreased, the cell ellipticity of cardiomyocytes gradually increased, which means that when the thickness of the base layer was smaller, the cardiomyocytes culture thereon were more mature.

[Evaluation of the Effect of the Base Layer with Microgrooves on Cardiomyocytes]

The base layer of the cell culture device provided by the present invention may further include elongated microgrooves, and the microgrooves may also be arranged in parallel or concentrically. In this evaluation, the width and spacing of the microgrooves were 20 μm, the depth was 4 μm, and the microgrooves were formed on the base layer with different thicknesses as described above. The evaluation of high-density cultured cardiomyocytes was performed, please refer to Examples 11-14 shown in Table 3, and the sarcomere length of cardiomyocytes was used as the judgment standard.

TABLE 3

| | Material | Thickness (μm) | Cell density (cells/well) | Sarcomere length (μm) |
|---|---|---|---|---|
| Example 11 | PP | 75 | 40000 | 1.86 |
| Example 12 | PP | 30 | 40000 | 1.90 |
| Example 13 | PP | 18 | 40000 | 1.81 |
| Example 14 | PS | 10 | 40000 | 1.91 |

Figure 8:
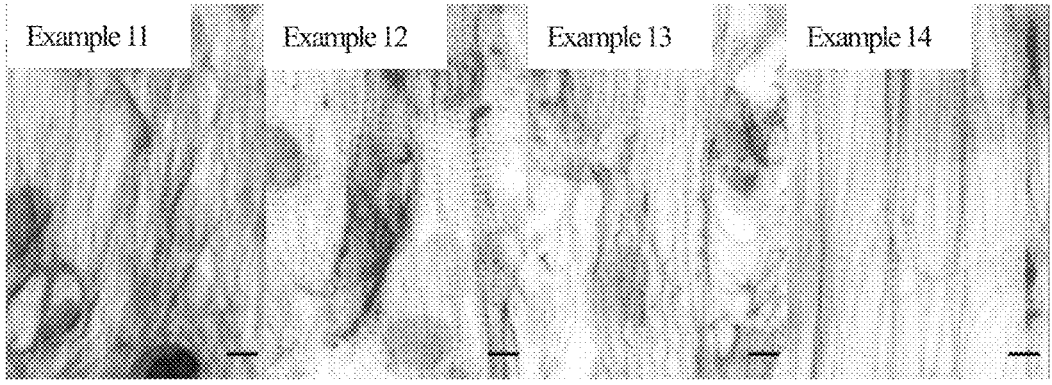
FIG. 8 shows the fluorescent images of the cells of Examples 11 to 14.

Please refer to the fluorescence images shown in FIG. 8 (scale bar=10 μm), it can be seen that cardiomyocytes grow along the extension direction of the microgrooves and produce relatively complete bonds. After comparing the sarcomere lengths of cells in Examples 1 to 5 without microgrooves, it can be found that in the base layer of 75 μm, the sarcomere length of cardiomyocytes cultured on the base layer with microgrooves increased from 1.75 μm to 1.86 μm, which was about 6.3% increase; in the base layer of 30 μm, the sarcomere length of cardiomyocytes cultured on the base layer with microgrooves increased from 1.79 μm to 1.90 μm, which was about 6.2% increase; and in the base layer of 10 μm, the sarcomere length of cardiomyocytes cultured on base layer with microgrooves increased from 1.79 μm to 1.91 μm, which was about 6.7% increase. The main function of the microgrooves was to reduce the second moment of inertia and flexural rigidity of the base layer to a lower value by changing the cross-sectional shape of the base layer to provide a base layer with higher flexibility and bending ability. The microgrooves also guided the myocytes to be arranged into a long and narrow structure. The addition of the microgroove structure had a significant effect on the sarcomere length of the cardiomyocytes for the base layer of different thicknesses, which can promote the maturity of the cardiomyocytes and improve the compliance of the base layer.

Next, the effect of the base layer including microgrooves with different thicknesses on the cardiomyocytes cultured at low density was evaluated. Please refer to Examples 15-18 shown in Table 4, the sarcomere length, the cell area, and the cell ellipticity were used as judgment standards.

TABLE 4

|  | Material | Thickness (μm) | Cell density (cells/well) | Sarcomere length (μm) | Cell area | Cell ellipticity |
|---|---|---|---|---|---|---|
| Example 15 | PP | 75 | 10000 | 1.68 | 2751.3 | 0.81 |
| Example 16 | PP | 30 | 10000 | 1.67 | 2561.4 | 0.85 |
| Example 17 | PP | 18 | 10000 | 1.69 | 2691.1 | 0.87 |
| Example 18 | PS | 10 | 10000 | 1.70 | 2450.7 | 0.86 |

Figure 9:
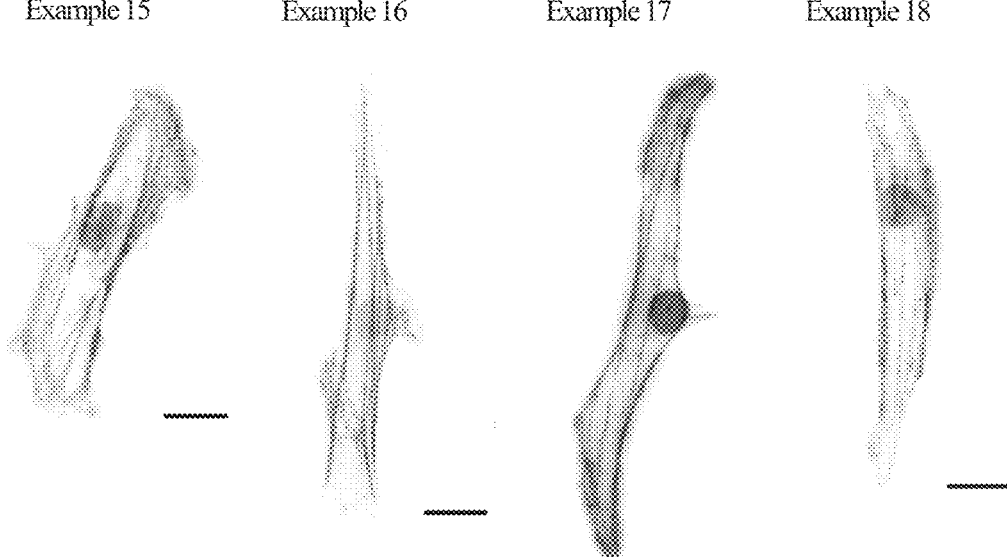
FIG. 9 shows the fluorescent images of the cells of Examples 15 to 18.
Figure 10:
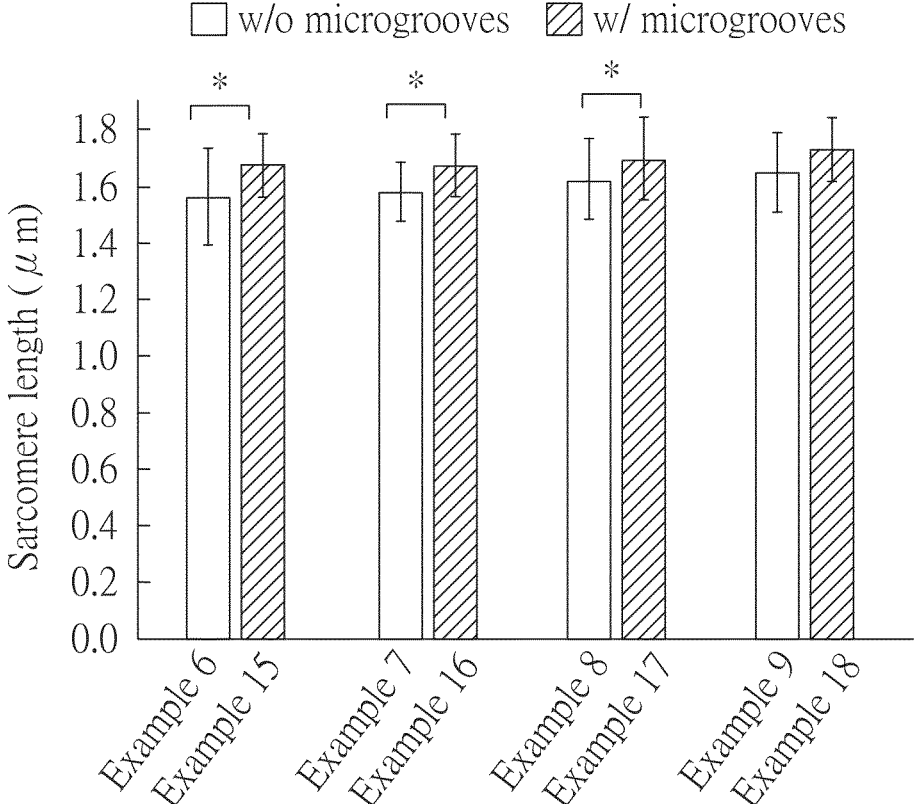
FIG. 10 shows measured sarcomere lengths of the cells of Examples 6 to 9 and 15 to 18.
Figure 11:
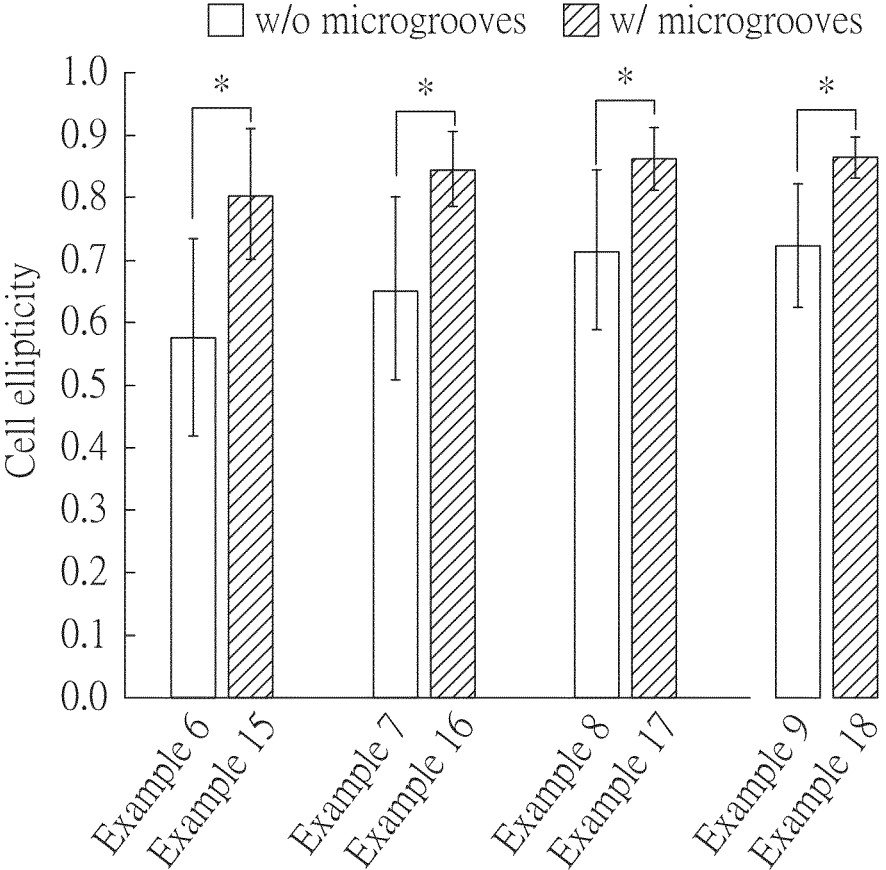
FIG. 11 shows the cell ellipticity of the cells of Examples 6 to 9 and 15 to 18.

Please refer to the fluorescence images of Examples 15 to 18 shown in FIG. 9 (scale bar=20 μm), and the sarcomere length of the cells of Examples 6 to 9 (without microgrooves) and 15 to 18 (with microgrooves) shown in FIG. 10. It can be found that in the base layer of 75 μm, the sarcomere length of the cardiomyocytes cultured after adding microgrooves increased from 1.64 μm to 1.68 μm, which was 2.4% increase; in the base layer of 30 μm, the sarcomere length of the cardiomyocytes cultured after adding microgrooves remained at 1.67 μm; in the base layer of 18 μm, the sarcomere length of the cardiomyocytes cultured after adding microgrooves increased from 1.67 μm to 1.69 μm, which was 1.2% increase; and in the base layer of 10 μm, the sarcomere length of the cardiomyocytes cultured after adding microgrooves increased from 1.67 μm to 1.70 μm, which was 1.8% increase. Accordingly, the base layer of different thicknesses can have a significant effect on the sarcomere length of cardiomyocytes whether the microgrooves were included or not. Next, please refer to the cell ellipticity of Examples 6 to 9 (without microgrooves) and 15 to 18 (with microgrooves) shown in FIG. 11; the comparison results show that the microgrooves have a significant impact on the cell ellipticity. Comparing to the flat base layer (without microgrooves), the cardiomyocytes cultured on base layers with microgrooves were more mature.

[Evaluation of the Effect of Different Thicknesses of the Base Layer on Cardiomyocyte Maturation]

To observe the maturation of cardiomyocytes cultured on base layers of different thicknesses, the performance of calcium ion waves of human-induced pluripotent stem cell differentiated cardiomyocytes after 15 days of culture in different base layers was investigated in this evaluation. The base layer of Example 19 was made of polyvinyl chloride (PVC) with a thickness of 10 μm, the base layer of Example 20 was made of PVC with a thickness of 5 μm, and in Comparative Examples 3 and 4, the base layers were respectively made of PMMA and PDMS with a thickness of 1 mm.

Figure 12:
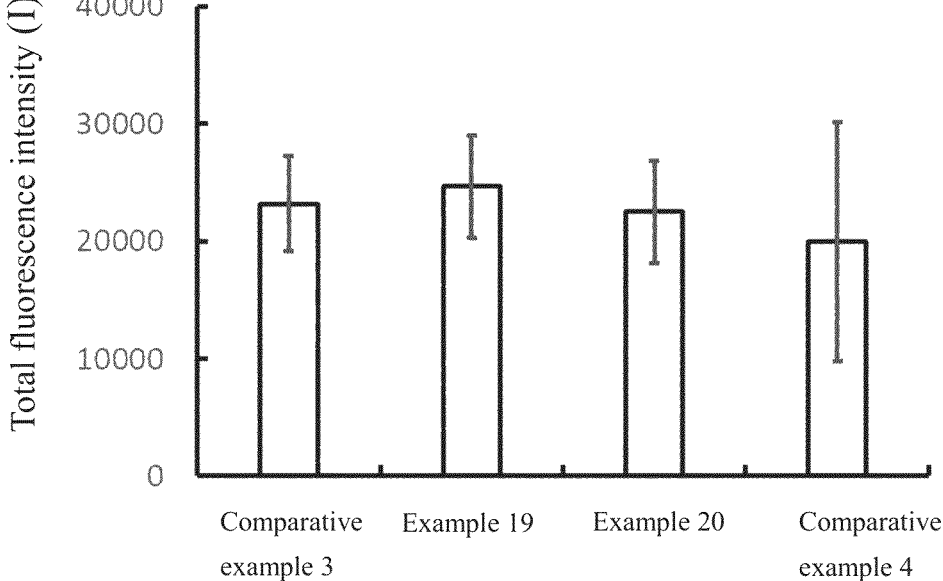
FIG. 12 shows the total fluorescence intensity of calcium ion wave in cardiomyocytes of Examples 19-20 and Comparative examples 3-4.
Figure 13:
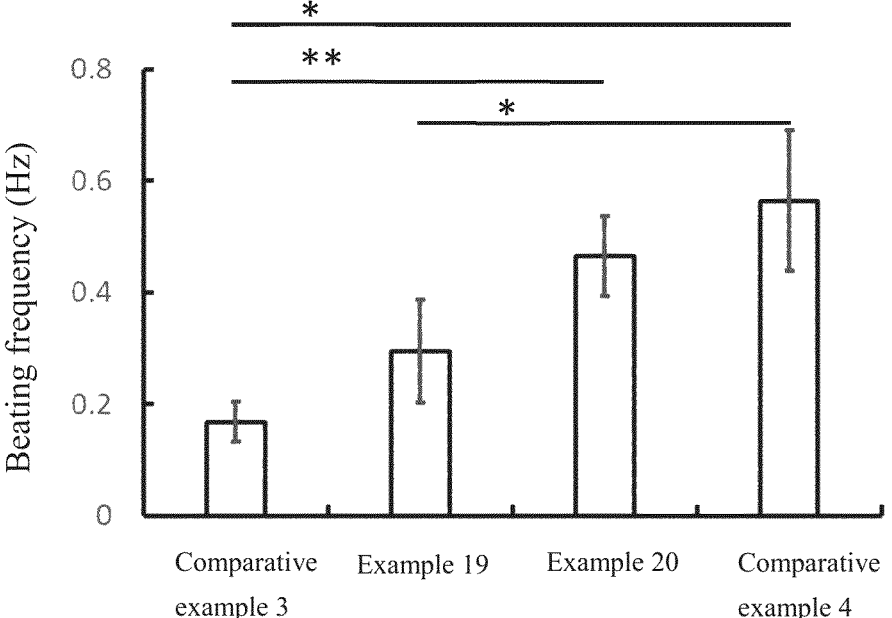
FIG. 13 shows the beating frequency of cardiomyocytes of Examples 19-20 and Comparative examples 3-4.

The results of the evaluations were shown in FIG. 12 and FIG. 13. FIG. 12 was the total fluorescence intensity of the cardiac calcium ion wave, and FIG. 13 was the comparison result of the beating frequency of the cardiac muscle. According to the results, there was no significant difference in the total fluorescence intensity of calcium ion waves between Examples 19 to 20 and Comparative examples 3 to 4. In contrast, the beating frequency of cardiomyocytes increased with the decrease of the thickness of the base layer. This experiment proved that the use of plastic thin-film as the base layer of the cell culture device can compensate for the tissue stiffness compared to the in vivo environments and provide a better culture environment and promotes the development of cells into mature cells and muscle tissue.

Based on the above evaluation results, when cardiomyocytes were cultured in a high-density environment, the cells interacted with each other. Mature cardiomyocytes are connected to form myocardial tissue and promote the increase in cell sarcomere length. As the thickness of the base layer decreases, especially when the thickness of the basal layer was 5 μm, the phenomenon of increasing the cell sarcomere length was significant. Therefore, it is verified that when the thickness of the base layer is reduced, the bending deformation of the base layer will increase when the cardiomyocytes contract on the base layer. The better cell culture conditions can be achieved by solving the problem of high stiffness of the base layer. When the microgrooves are introduced to the base layer, the bending ability and flexibility of the base layer can be further improved. At the same time, the cardiomyocytes tend to be connected and arranged with each other, and the cell sarcomere length thereof can be significantly increased, so that the maturity of the cardiomyocytes can be greatly improved. When cardiomyocytes were grown in a low-density environment, the change in cell sarcomere length of cardiomyocytes was similar to that of cardiomyocytes cultured in a high-density condition. In terms of cell area, it can be seen that when the thickness of the base layer decreased, the morphology of cardiomyocytes became slender as the mature cells, and the homogeneity was also improved. In terms of cell ellipticity, it can be seen that as the thickness of the base layer decreased, the cell ellipticity gradually increased. When microgrooves were added to the base layer, the maturity of cardiomyocytes was improved.

In summary, the cell culture device provided by the present invention is flexible and can be designed with microgrooves, which is beneficial for improving the maturity of myocytes. The high flexibility achieved by reducing the thickness of the base layer can imitate the in vivo growth conditions of myocytes, so that the myocytes cultured in vitro have a similar growth environment, and the deformation amount and contraction distance can be increased during contraction.

The cell culture device provided by the present invention is not limited for culturing cardiomyocytes, skeletal myocytes, smooth myocytes, and various adherent cells may be cultured thereon.

What is claimed is:

1. A cell culture device, comprising:
a cavity including an opening and a bottom;
a base layer disposed at the bottom of the cavity and closing the bottom, wherein a thickness of the base layer is between 1 μm to 100 μm, a second-moment of inertia of the base layer is lower than $6\times10^6$ μm$^4$, and a resultant flexural rigidity of the base layer is between is $1\times10^{-6}$ Pa·m$^4$ to 0.02 Pa·m$^4$; and
a hollow spacer disposed under the base layer and contacting with an edge of the base layer;
wherein the hollow spacer is configured to prevent the base layer from contacting any surface thereunder and allows the base layer to generate out-of-plane strain during a cell culture process;
wherein the base layer is made of a plastic film at least one selected from the group consisting of polymethyl methacrylate, polypropylene, polystyrene, polyethylene, polyethylene terephthalate, polyvinyl chloride, polydi-
methylsiloxane, polyurethane, polyacrylamide, and
mixtures thereof;

wherein the base layer further includes a plurality of
microgrooves, wherein each one of the plurality of
microgrooves are arranged adjacent and parallel to each
other.

2. The cell culture device as claimed in claim 1, wherein
a width of each of the microgrooves is 5 μm to 50 μm, and
a gap between the adjacent microgrooves is 5 μm to 50 μm.

3. The cell culture device as claimed in claim 1, wherein
a depth of each of the microgrooves is between 1 μm to 10
μm.

4. The cell culture device as claimed in claim 1, further
comprising a coating layer formed on the base layer, wherein
the coating is at least one selected from the group consisting
of matrix hydrogel, collagen, fibronectin, laminin, gelatin,
and mixtures thereof.

5. A cell culture multi-well plate, comprising:
a main body including an accommodating space and a
first surface; and
a plurality of the cell culture device claimed in claim 1,
each of the plurality of cell culture devices is disposed
in the accommodating space;
wherein the opening of the cavity of each of the plurality
of cell culture devices is formed on the first surface.

\* \* \* \* \*